United States Patent
Pasqualucci et al.

(10) Patent No.: US 6,318,616 B1
(45) Date of Patent: Nov. 20, 2001

(54) SURGICAL FASTENER APPLIER

(75) Inventors: Joseph Pasqualucci, North Haven; Thomas Wenchell, Durham, both of CT (US)

(73) Assignee: United States Surgical, Norwalk, CT (US)

( * ) Notice: Subject to any disclaimer, the term of this patent is extended or adjusted under 35 U.S.C. 154(b) by 0 days.

(21) Appl. No.: 09/422,381

(22) Filed: Oct. 21, 1999

Related U.S. Application Data (60) Provisional application No. 60/105,365, filed on Oct. 23, 1998.

(51) Int. Cl.$^7$ .................................................. A61B 17/068
(52) U.S. Cl. .......................... 227/83; 227/19; 227/176.1; 227/156
(58) Field of Search .............................. 227/83, 121, 119, 227/155, 19, 120, 175.1, 176.1, 156

(56) References Cited

U.S. PATENT DOCUMENTS

| Re. 28,932 | 8/1976 | Noiles et al. . | | |
|---|---|---|---|---|
| 3,618,842 | 11/1971 | Bryan . | | |
| 3,638,847 | 2/1972 | Noiles et al. . | | |
| 3,643,851 | 2/1972 | Green et al. . | | |
| 3,717,294 | 2/1973 | Green . | | |
| 3,837,555 | 9/1974 | Green . | | |
| 3,949,924 | 4/1976 | Green . | | |
| 4,127,227 | 11/1978 | Green . | | |
| 4,204,623 | 5/1980 | Green . | | |
| 4,364,507 | * | 12/1982 | Savino | 227/83 |
| 4,391,401 | * | 7/1983 | Moshofsky | 227/19 |
| 4,410,125 | 10/1983 | Noiles et al. . | | |
| 4,619,391 | * | 10/1986 | Sharkany et al. | 227/83 |
| 4,645,111 | * | 2/1987 | Larrabee et al. | 227/83 |
| 4,669,647 | * | 6/1987 | Storace | 227/83 |
| 4,789,090 | * | 12/1988 | Blake, III | 227/19 |
| 4,991,763 | * | 2/1991 | Storace | 227/119 |
| 5,217,472 | 6/1993 | Green et al. . | | |

* cited by examiner

*Primary Examiner*—Scott A. Smith (57) ABSTRACT

Surgical stapler including a longitudinal body having a handle portion and a trigger portion pivotally mounted to the handle portion. The surgical stapler including a cartridge assembly having a plurality of formable staples therein. The staples being formable through actuation of the trigger portion of the longitudinal body. The cartridge assembly includes an upper chassis assembly having a centrally disposed channel. The channel accommodating a reciprocating pusher follower and a reciprocating pusher plate. The pusher plate being coupled to the pusher follower and reciprocally advancable against an anvil plate. The pusher plate forming at least one of a plurality of staples around an anvil tip of the anvil plate. The cartridge assembly also including a lower track portion coupled to the upper chassis assembly. The lower track portion including a plurality of channels and ridges for receiving end points of the plurality of staples, wherein at least one of the plurality of staples is advancable between the pusher plate and the anvil plate for forming the at least one of the plurality of staples around the anvil plate.

28 Claims, 10 Drawing Sheets

SURGICAL FASTENER APPLIER

This application claims priority from U.S. Provisional Application Serial No. 60/105,365, filed Oct. 23, 1998.

BACKGROUND

1. Technical Field

The present disclosure generally relates to surgical fastener appliers, and more particularly, is directed to surgical fastener appliers of the type which are used for closing wounds in skin and fascia tissue.

2. Background of the Related Art

The placement of clips and staples by surgical fastener appliers for closing wounds in skin and fascia tissue is well known. By way of example, U.S. Pat. No. 4,410,125 to Noiles et al. discloses a surgical stapler apparatus with a staple pusher plate for forming staples around tissue. The staples are fed successively into instrument jaws and cammed closed around skin or fascia tissue by the pusher plate. The staples are stored in the instrument in a longitudinal stack which is substantially parallel to the longitudinal axis of the instrument. The distal-most staple in the stack is applied to the tissue by being bent or formed around an anvil tip of an anvil plate. An actuator adjacent the proximal end of the pusher plate reciprocates the pusher plate along its trajectory so that the distal end of the pusher plate advances the distal-most staple to the anvil and forms the staple around the anvil.

Furthermore, the Noiles et al. surgical stapler includes a metal staple track for carrying the stack of staples. The metal staple track is covered along an outer portion thereof with a plastic bottom or lower housing cover which forms an exterior portion of the surgical stapler. The staples are maintained at an inclined position relative to the metal staple track with staple tips in sliding contact with the metal track. As the pusher plate is cammed toward the anvil, the distal end portion of the pusher plate slides against and beyond a distal end portion of the metal track forming a nose gap space between an underside of the anvil plate and the distal end portion of the metal track. The nose gap space keeps the pusher plate free from galling or binding with the metal track as repeated staples are fired from the stapler.

While the Noiles et al. surgical stapler is an excellent design, the staple cartridge includes a lower portion having two separate parts, namely, the metal staple track and lower housing which increases the cost of manufacture. Additionally, the Noiles et al. surgical stapler is designed such that the staples are maintained at an angle relative to the longitudinal base of the metal track with staple tips in contact with the metal track as the staples are presented for firing. Thus, the metal track serves as a buffer and guide for movement of the staples along the firing track. Finally, a nose gap space exists in order to prevent the pusher plate from galling or binding with the metal track as the pusher plate slides between the underside of the anvil plate and the end portions of the metal track.

Accordingly, a need exists in the art for a new and improved surgical stapler which effectively fires clips/staples into skin or fascia tissue which is formed with fewer parts, provides smooth operation and results in lower manufacture cost.

Therefore, the embodiments herein disclosed throughout the present disclosure achieve the intended purposes, objects, and advantages through a new, useful and unobvious combination of component elements, with the use of a minimum number of functioning parts, at a reasonable cost to manufacture, and by employing readily available materials.

Figure 1:
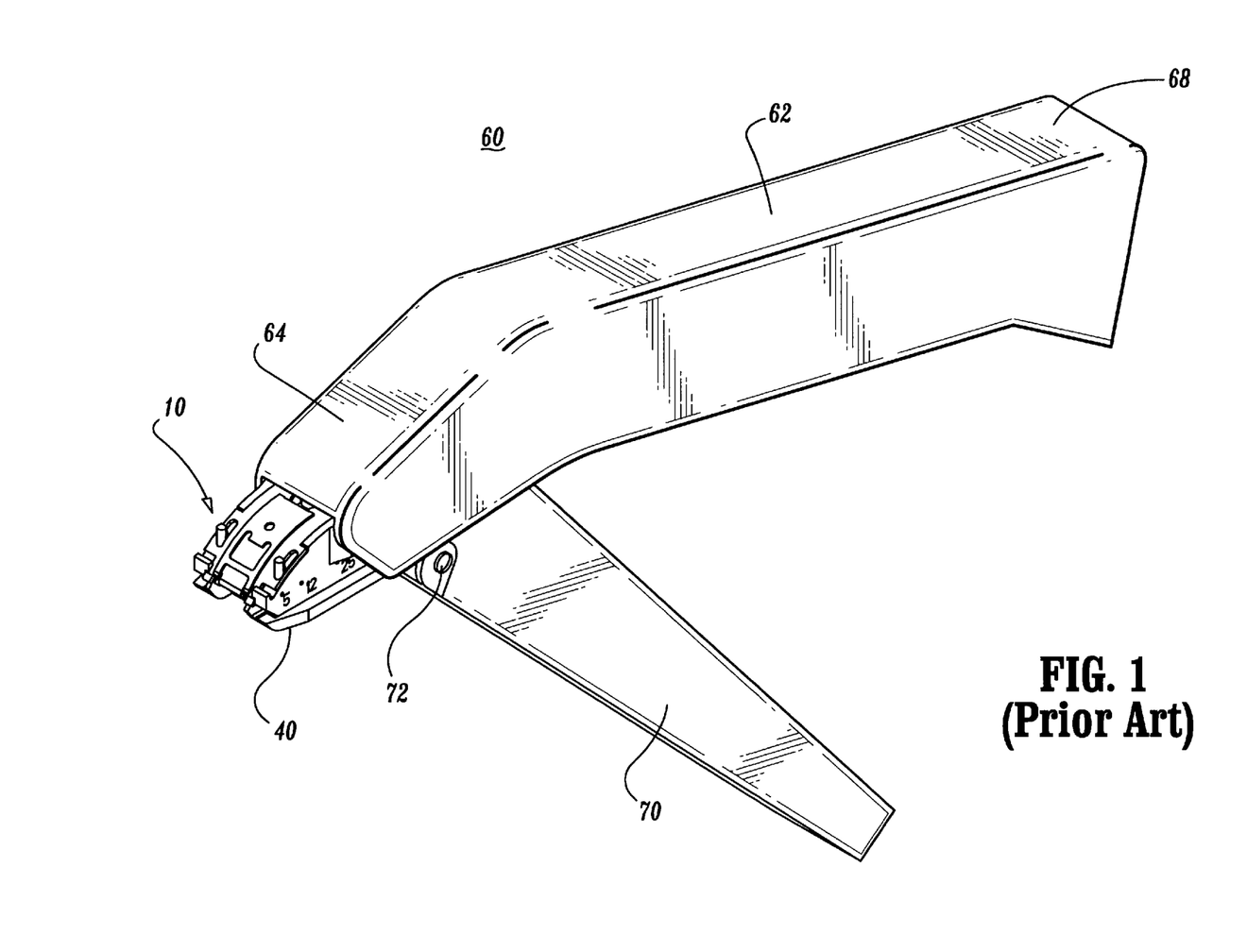
FIG. 1 is a perspective view illustrating a prior art surgical stapler.
Figure 2:
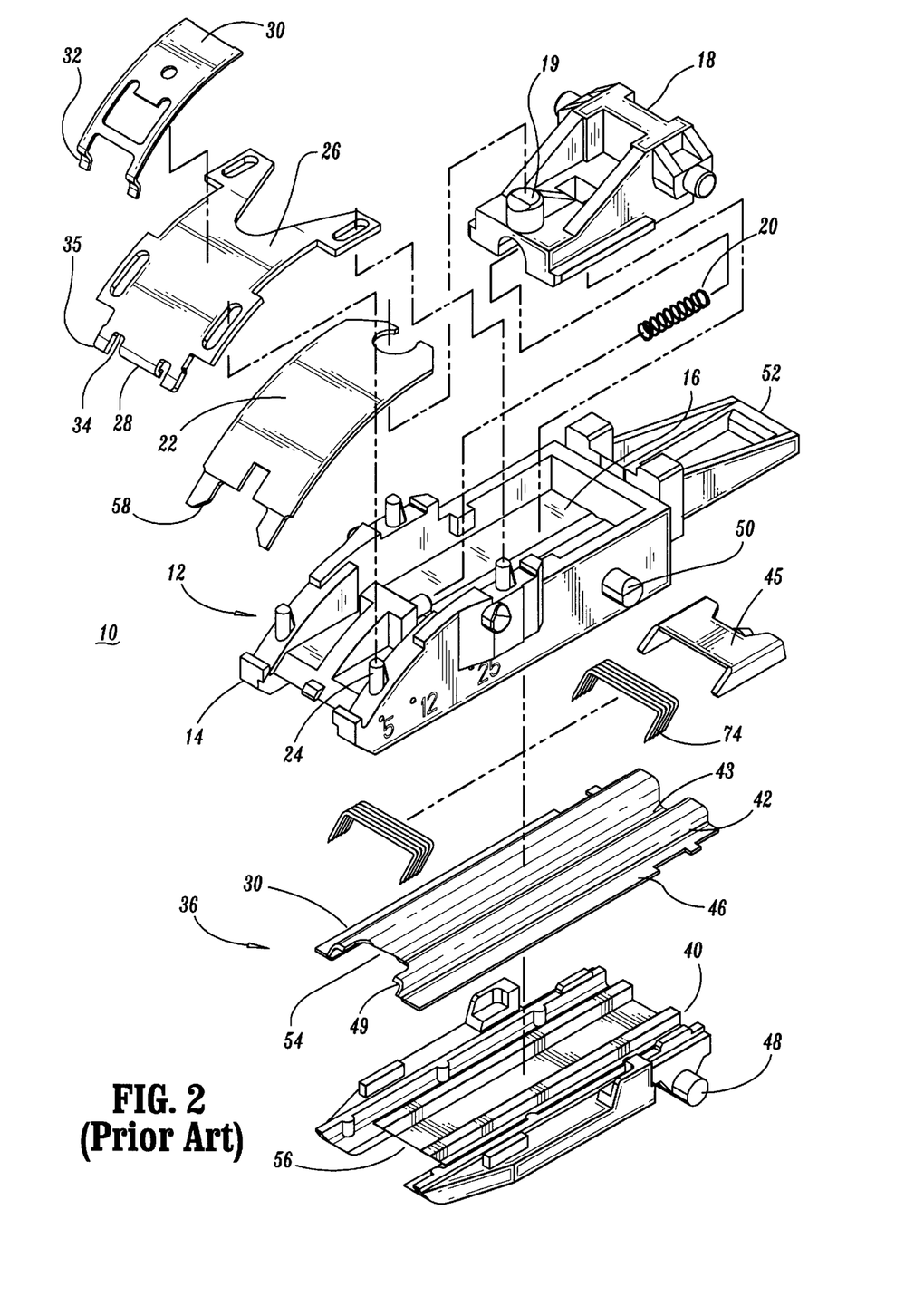
FIG. 2 is an exploded view illustrating a prior art cartridge assembly for the surgical stapler of FIG. 1.

With particular reference to FIGS. 1 and 2, there is illustrated a perspective view (FIG. 1) of a prior art surgical stapler 60, namely, the Royal Auto Suture (™), available from United States Surgical Corporation of Norwalk, Connecticut and an exploded view (FIG. 2) of a prior art cartridge assembly 10 for use in a portion of the surgical stapler 60. Surgical stapler 60 is made up of central body part 62, top cover 64, lower housing 40 and proxinally extending portion 68. Proximally extending portion 68 is sized and shaped to fit comfortably in the palm of an operator's hand, with trigger handle 70 being within the reach of one or more fingers of that hand. Trigger handle 70 is pivotally mounted on the central body part 62 by way of pivotal axis 72 which includes projections 48 extending from lower housing 40.

As best illustrated in FIG. 2, the cartridge assembly 10 contains a plurality of staples 74 formed in a stack along a bottom portion thereof. The cartridge assembly 10 includes an upper chassis assembly 12 which includes cartridge housing 14. Cartridge housing 14 is coupled to central body part 62 of surgical stapler 60 via projections 50. Cartridge housing 14 includes a central channel 16 for receiving pusher follower 18 and compression coil 20. Pusher follower 18 is biased distally by compression coil 20 and includes securing projection 19 for securing reciprocally advancing pusher plate 22. Both the pusher follower 18 and pusher plate 22 move distally against the bias of compression coil 20 within central channel 16. Pusher plate 22 includes staple forming projections 58 which, when distally advanced around a periphery of anvil tip 28 (to be described later herein), form staple 74 into tissue. Cartridge housing 14 further includes a proximally located tab projection 52 which is coupled to an underside of central body part 62. Tab projection 52 acts as a backstop for a proximal portion of a compression spring (not shown).

Along a top portion of upper chassis assembly 12 is positioned an anvil plate 26 which is affixed onto projections 24 of cartridge housing 14. Anvil plate 26 includes anvil tip 28 which is used to form staples 74 as pusher plate 22 is distally advanced against an underside of anvil tip 28. Anvil plate 26 further includes anvil plate projections 35 and grooves 34. Pusher plate 22 forms an arc of a circle as it is distally advanced along the underside of anvil plate 26 toward anvil tip 28. A wrap portion 30 is snap fit over anvil plate 26 and includes projections 32 which fit into the grooves 34 between anvil plate projections 35. The projections 32 are used to bias staples 74 into a staple forming position as each staple 74 is formed around anvil tip 28 and corresponding tissue.

The cartridge assembly 10 further includes a lower chassis assembly 36 having a metal staple track 38 and lower housing 40. Lower chassis assembly 36 is coupled to an underside of upper chassis assembly 12 and secures the plurality of staples 74 therebetween. Metal staple track 38 is fitted between cartridge housing 14 and lower housing 40 and includes channels 42 and flat portions 46 for longitudinally storing a stack of staples 74. Metal staple track 38 further includes a longitudinally spaced central depression 43 over which is received staple follower 45 and associated compression spring (not shown). The ends of staples 74 slide along the flat portions 46 of metal staple track 38 as staple follower 45 and associated compression spring distally bias the stack of staples 74 toward anvil tip 28. Lower housing 40 includes proximally located projections 48 to which trigger handle 70 is pivotally mounted. Along proximal portions of metal staple track 38 and lower housing 40 include cut out window portions 54 and 56, respectively. The window portions 54 and 56 provide an open space along the distal end portion of the underside of the lower chassis assembly 36 and allow ample space for the proper formation of the staples 74 around the tissue.

In the formation of staple 74 around tissue, pusher plate 22 and staple forming projections 58 are advanced distally of anvil tip 28 and distal end portions 49 of metal staple track 38. Such advancement of pusher plate 22 between anvil plate 26 and distal end portions 49 of metal staple track 38 causes frictional contact between pusher plate 22, anvil plate 26 and metal staple track 38. To this effect, there exists a nose gap space between an underside of the projections 35 of anvil plate 26 and the distal end portions 49 of metal staple track 38. This nose gap space keeps the pusher plate 22 free from galling or binding with metal staple track 38 as repeated staples are fired from the surgical stapler 60.

The stack of staples 74 contained within the lower chassis 36 and along the metal staple track 38 are maintained at an incline relative to the metal staple track 38. The inclined positioning of staples 74 serves to properly align the staples 74 for firing. The inclined position of the staples 74 is generally equal to the inclination of pusher plate 22 as pusher plate 22 slides under anvil plate 26 and around the periphery of anvil tip 28. With the staples 74 in this inclined position relative to the metal staple track 38, the staple tips are in sliding contact with metal staple track 38 as they are distally advanced toward the firing position.

SUMMARY

The present disclosure is directed to an improved surgical fastener applier for closing wounds in skin and fascia tissue. The surgical stapler is simpler in construction, employs less parts and includes a lower cost of manufacture.

Accordingly, a surgical fastener applier is disclosed and preferably includes a longitudinal body having a handle portion and a trigger portion pivotally mounted to the handle portion. The surgical fastener applier further includes a cartridge assembly having a plurality of formable staples therein. The staples being formable through actuation of the trigger portion of the longitudinal body. The cartridge assembly includes an upper chassis assembly having a centrally disposed channel. The channel accommodates a reciprocating pusher follower and a reciprocating pusher plate. The pusher plate is coupled to the pusher follower and reciprocally advancable against an anvil plate. The pusher plate forms at least one of a plurality of staples around an anvil tip of the anvil plate.

The cartridge assembly also includes a lower track portion coupled to the upper chassis assembly. The lower track portion includes a plurality of channels and ridges for receiving end points of the plurality of staples, wherein at least one of the plurality of staples is advancable between the pusher plate and the anvil plate for forming the at least one of the plurality of staples around the anvil plate. The lower track portion is preferably a monolithically formed thermoplastic material and includes angled distal end segments for slidingly receiving distal end projections of the pusher plate. The lower track portion preferably includes projections for pivotable mounting of the lower track to the trigger portion of the longitudinal body.

In preferred embodiments the pusher plate includes at least one protrusion along a distal end thereof. The protrusion acts to bias the at least one of the plurality of staples to a pre-fire position and preferably being in the shape of a dimple.

In other preferred embodiments the surgical stapler includes a staple follower for distally biasing the plurality of staples along at least two of the plurality of channels of the lower track portion.

BRIEF DESCRIPTION OF THE DRAWINGS

The objects and features of the present disclosure, which are believed to be novel, are set forth with particularity in the appended claims. The present disclosure, both as to its organization and manner of operation, together with further objectives and advantages may best be understood by reference to the following description, taken in connection with the accompanying drawings, in which:

DETAILED DESCRIPTION OF PREFERRED EMBODIMENTS

The preferred embodiments of the apparatus and methods disclosed herein are discussed in terms of closing wounds in skin and fascia tissue and the instrumentation therefore. The present disclosure is applicable to surgical staplers which are disposable and not intended to be reloaded and which are discarded after use in a surgical procedure or after the initial supply of staples is exhausted, as well as, surgical staplers which are permanent and which can therefore be reloaded with staples when an initial staple supply is exhausted.

In the discussion herein, the term "proximal", as is traditional, will refer to the portion of the structure which is closer to the operator, while the term "distal" will refer to the portion which is further from the operator.

Figure 3:
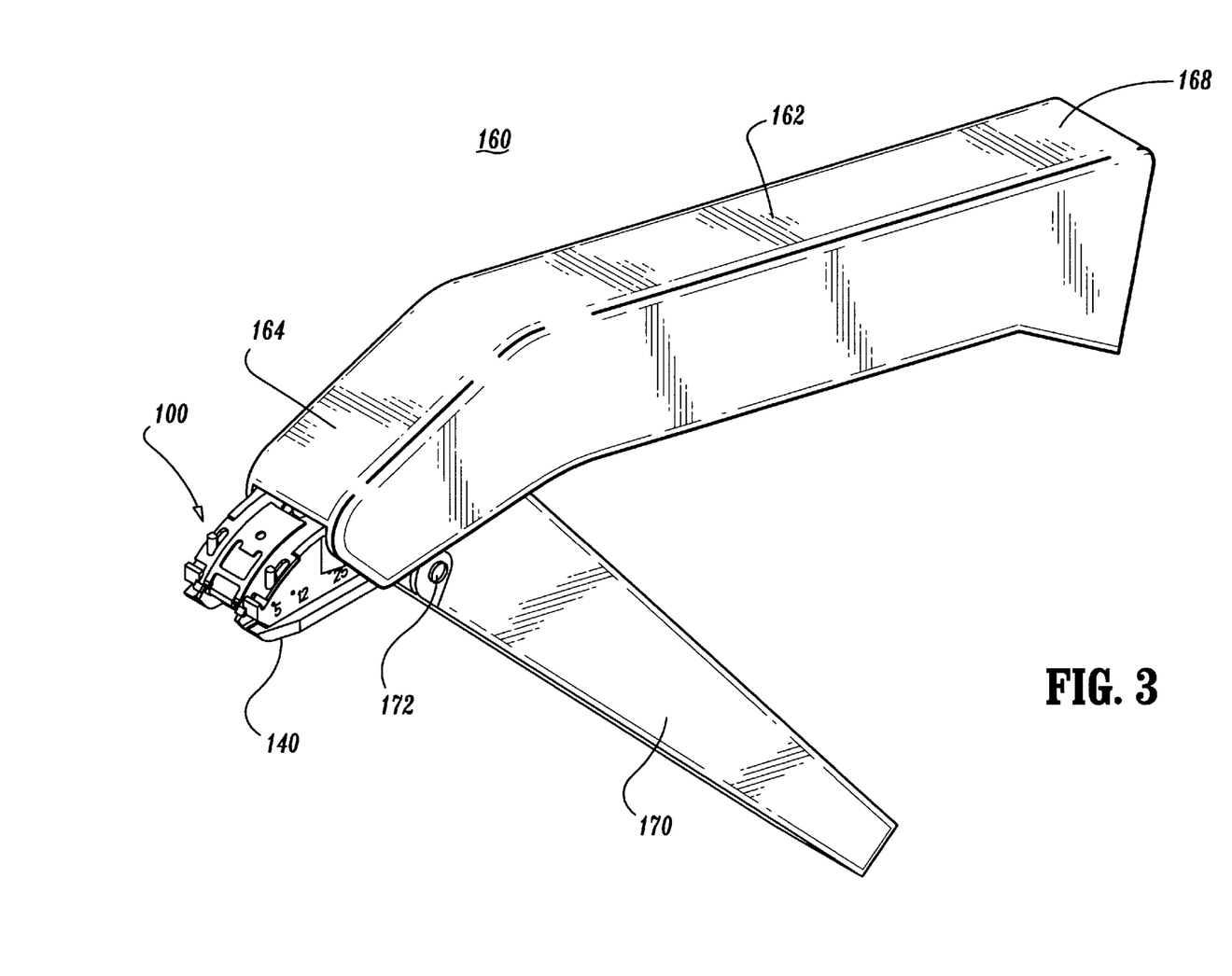
FIG. 3 is a perspective view illustrating a surgical stapler according to the present disclosure.
Figure 4:
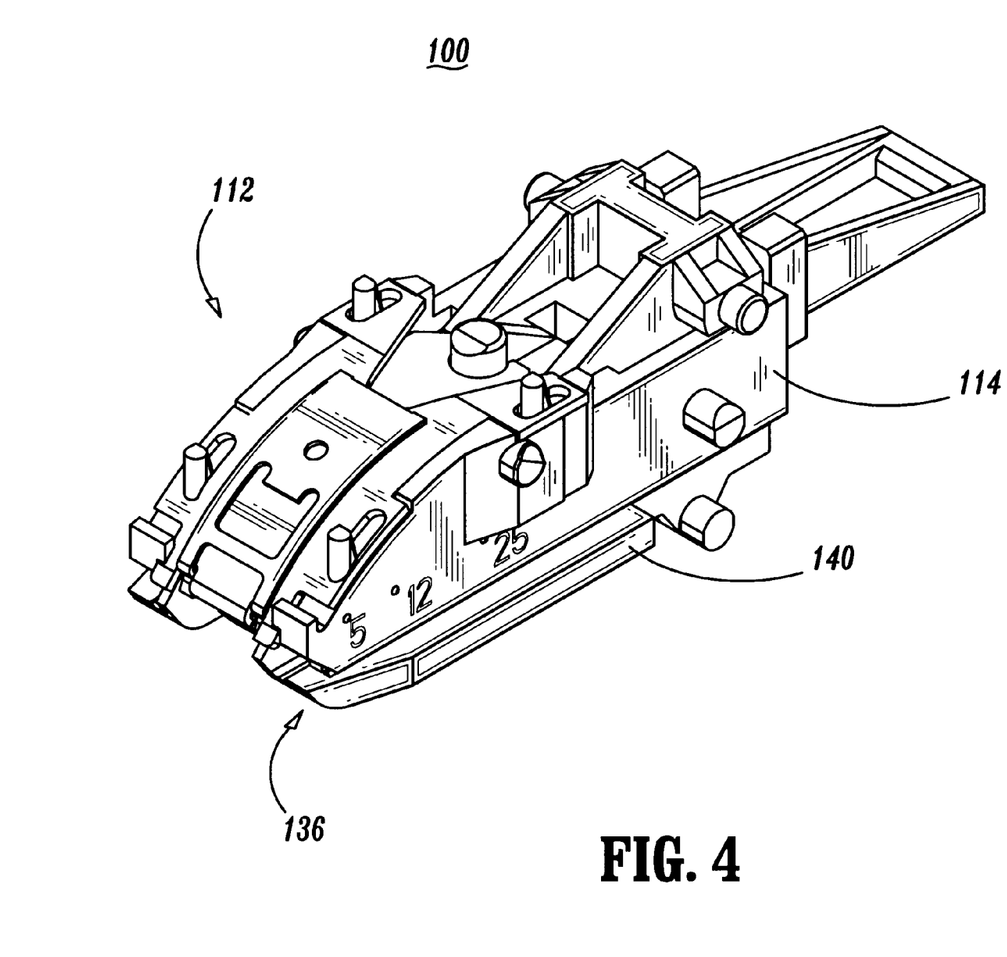
FIG. 4 is a perspective view illustrating a cartridge assembly for the surgical stapler of FIG. 3.
Figure 5:
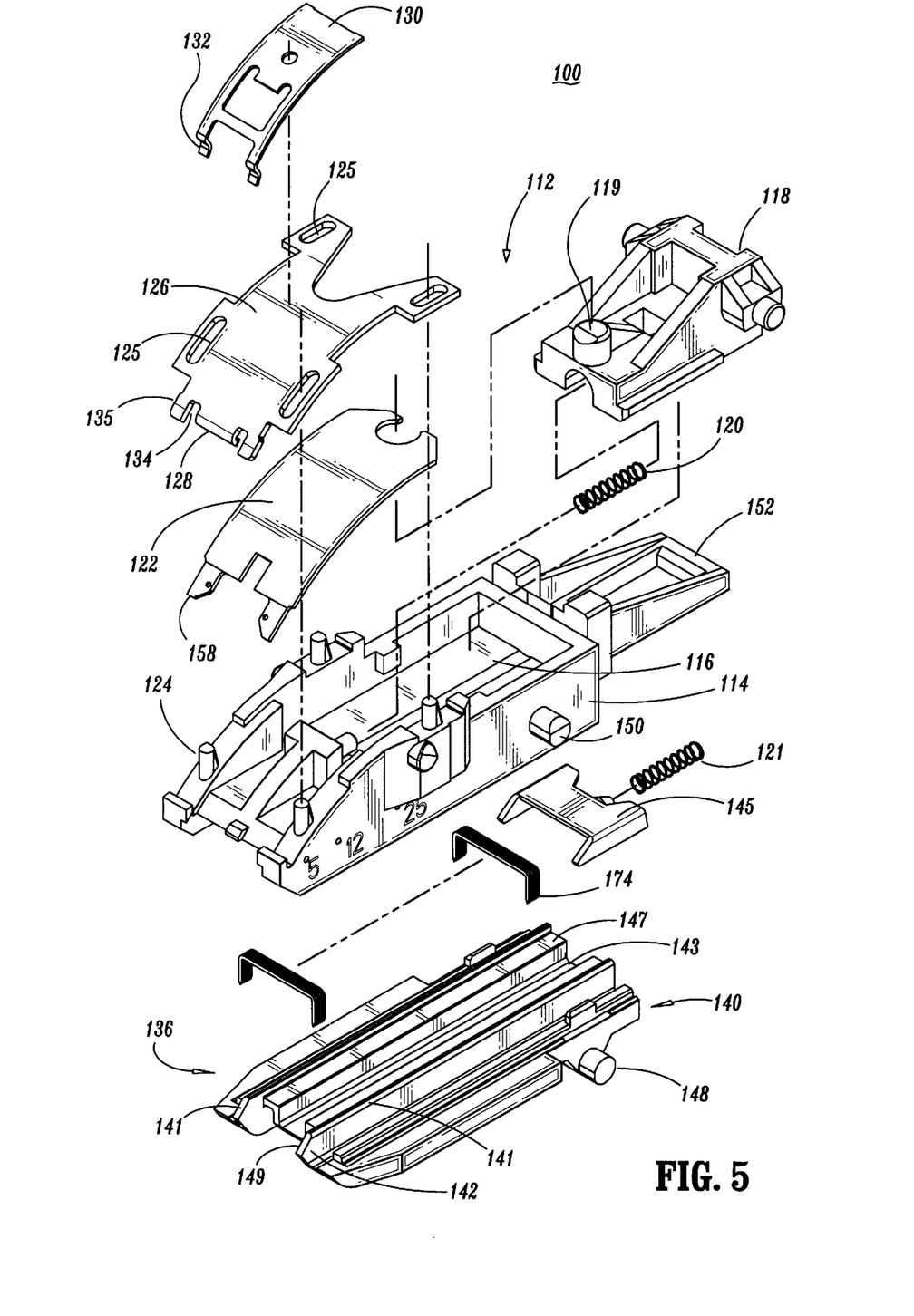
FIG. 5 is an exploded view illustrating the cartridge assembly of FIG. 4.

Reference will now be made in detail to the preferred embodiments of the disclosure, which are illustrated in the accompanying figures. Turning now to the figures, wherein like components are designated by like reference numerals throughout the various figures, attention is first directed to FIGS. 3–5 depicting a surgical stapler 160 and cartridge assembly generally designated by reference character 100. The surgical stapler and cartridge assembly is similar to the surgical stapler apparatus described in U.S. Pat. No. 4,410, 125 to Noiles et al., the entire contents of which are herein expressly incorporated by reference.

The overall structural and operational features of cartridge assembly 100 are very similar to those described above for cartridge assembly 10. Accordingly, the following description will focus on those features which are either unique to instrument 100 or are substantially different to corresponding elements of cartridge assembly 10.

With reference to FIGS. 3 and 4, surgical stapler 160 is made up of central body part 162, top cover 164, cartridge assembly 100, lower track 140 and proximally extending portion 168. Proximally extending portion 168 is sized and shaped to fit comfortably in the palm of an operator's hand, with trigger handle 170 being within the reach of one or more fingers of that hand. Trigger handle 170 is pivotally mounted on the central body part 162 by way of pivotal axis 172.

The surgical stapler 160 includes a cartridge assembly 100 with an upper chassis assembly 112 which includes cartridge housing 114. The cartridge assembly 100 further includes a lower chassis assembly 136 having of a lower track portion 140. Lower track portion 140 is preferably made of a thermoplastic material and is coupled to an underside of cartridge housing 114 forming therebetween staple channel areas 142, 143 (to be discussed later herein) which house a plurality of staples 174 to be applied to tissue.

With specific reference to FIG. 5, an exploded view illustrating the cartridge assembly according to the present disclosure is shown. The cartridge assembly 100 includes upper chassis assembly 112 having cartridge housing 114. Cartridge housing 114 is coupled to central body part 162 of surgical stapler 160 via projections 150. Cartridge housing 114 includes a central channel 116 for receiving pusher follower 118 and compression coil 120. Pusher follower 118 is biased along channel 116 by compression coil 120 and includes a securing projection 119 for securing pusher plate 122. In operation, pusher follower 118 and pusher plate 122 reciprocate within central channel 116. Pusher plate 122 includes staple forming projections 158. In the formation of staples 174 around tissue, the staple forming projections 158 are distally advanced around a periphery of anvil tip 128 of anvil plate 126 (to be described later herein). Cartridge housing 114 further includes a proximally located tab projection 152 which is coupled to an underside of central body part 162. Tab projection 152 acts as a backstop for a proximal portion of compression spring 121 (FIG. 10).

Along a top portion of upper chassis assembly 112 is positioned an anvil plate 126 which is affixed onto projections 124 of cartridge housing 114 through cut outs 125. Anvil plate 126 includes anvil tip 128, grooves 134 and projections 135 along a distal end portion thereof. Staples 174 are formed around anvil plate 128 as pusher plate 122 and staple forming projections 158 are advanced distally against the bias of compression coil 120 beyond the distal end of anvil plate 126. In forming staples 174 around tissue, pusher plate 122 moves through an arc of a circle as pusher plate 122 is distally advanced along the underside of anvil plate 126. A wrap portion 130 is snap fit over anvil plate 126 and includes projections 132 which fit into grooves 134 of anvil plate 126. The projections 132 are used to bias staples 174 into staple forming positions as each staple 74 is formed around anvil tip 128.

Figure 10:
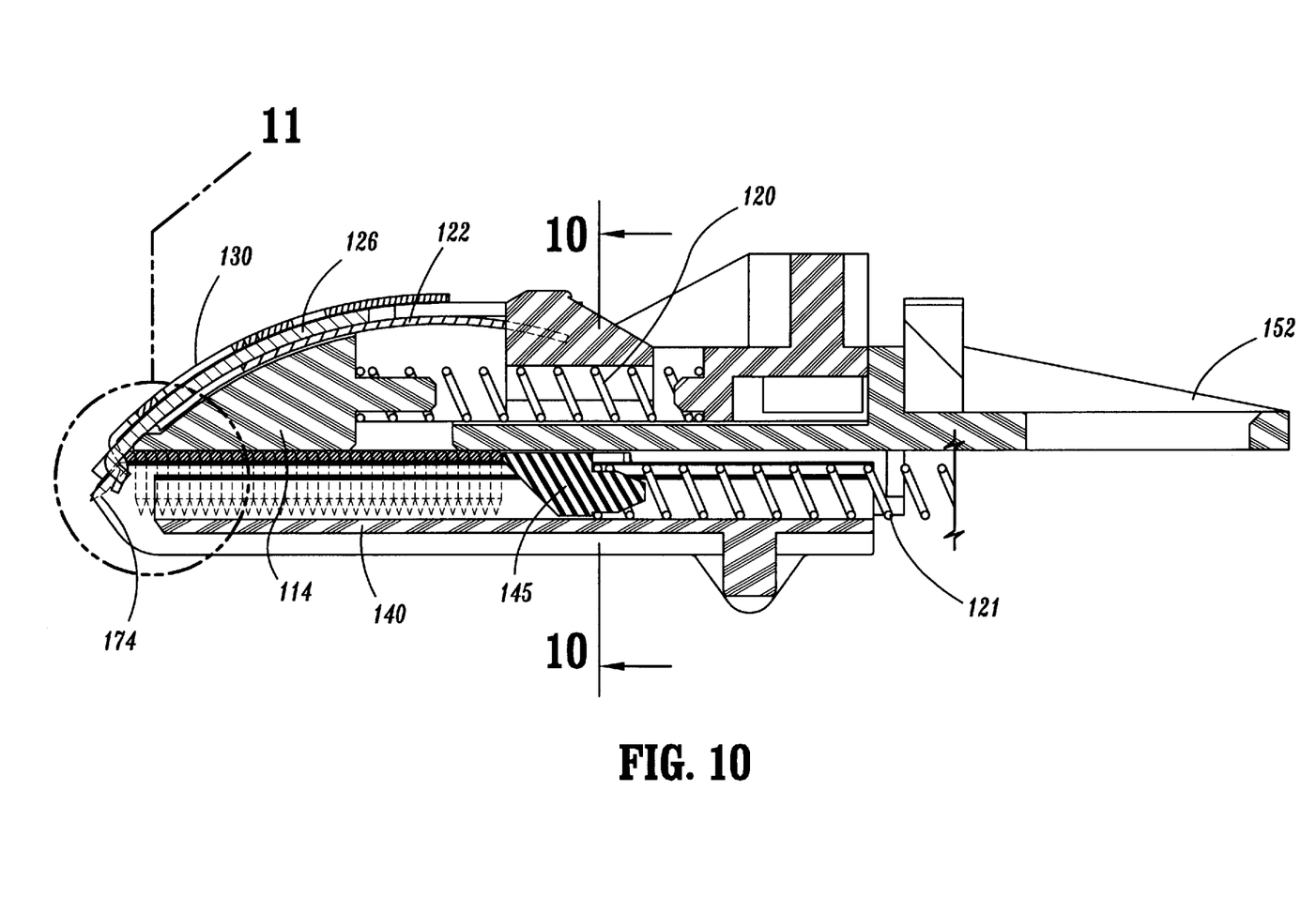
FIG. 10 is an enlarged cross-sectional view of the cartridge assembly according to the present disclosure.
Figure 11:
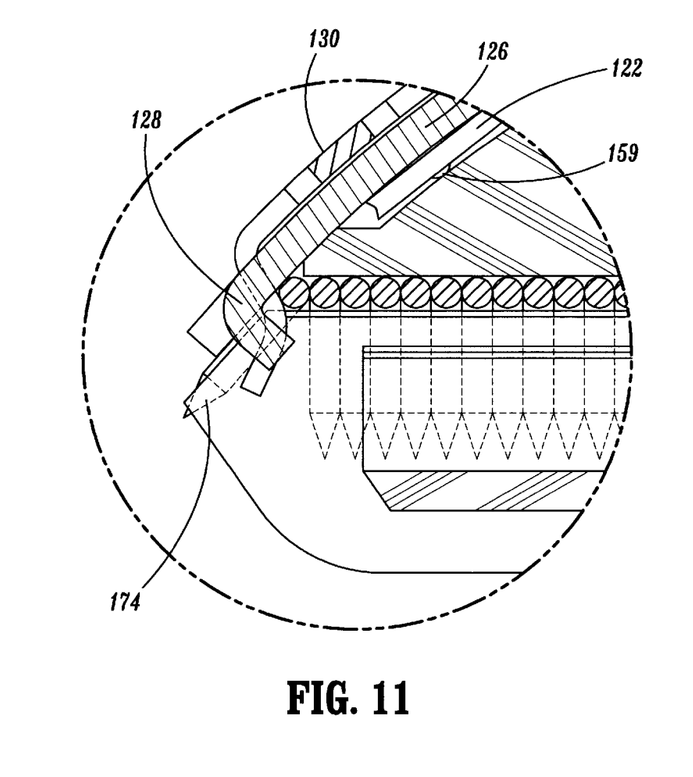
FIGS. 11–13 are sequential enlarged sectional views of the cartridge assembly of FIG. 10 taken along circled area 11 of FIG. 10 depicting the loaded, firing and reloading positions of the cartridge assembly according to the present disclosure.

As best seen in FIGS. 5 and 8–10, the cartridge assembly 100 of the present disclosure further includes a lower chassis assembly 136 having a lower track assembly 140. Lower track assembly 140 preferably has a unitary molded thermoplastic track which is coupled to an underside of upper chassis assembly 112. Lower track 140 includes proximally located projections or tabs 148 to which trigger handle 170 of surgical stapler 160 is pivotally mounted. Lower track 140 is designed to carry a stack of staples 174 along an upper portion 147 thereof. Upper portion 147 includes a staple carrying configuration having top ridges 141 and a central depression or channel 143. Side channels 142 are located along upper portion 147 for carrying ends of staples 174. As shown in FIGS. 10 and 11, the ends of staples 174 are spaced above the bases of side channels 142 of lower track 140. The staples 174 are distally biased along side channels 142 and over top ridges 141 by staple follower 145 and associated compression spring 121 (FIG. 10) which is connected at one end to staple follower 145 and at the other end to an underside of central body part 162 and tab projection 152. As staples 174 are being fired or formed around tissue, the ends of staples 174 are distally driven along channels 142 by staple follower 145 which is biased by compression spring 121.

In operation of surgical stapler 160, actuation of trigger handle 170 along pivotal axis 172 cams pusher follower 118 distally along channel 116. Pusher follower 118 drives pusher plate 122 arcuately and distally between an underside of anvil plate 126 toward anvil tip 128. Once reaching anvil tip 128, the pusher plate 122 forms staple 174 wherein projections 158 are advanced to a point distal of anvil tip 128 and angled distal ends 149 of lower track 140. Unlike the prior art surgical stapler of FIGS. 1 and 2, the movement of pusher plate 122 between the underside of anvil plate 126 and lower track 140 does not cause appreciable frictional contact between pusher plate 122, anvil plate 126 and lower track 140. Similarly, the present disclosure provides for the substitution of a single lower track 140 for the metal staple track 38 and lower housing 40 disclosed in the prior art. This substitution provides for a minimal nose gap space between an underside of the anvil plate projections 135 and the angled distal ends 149 of lower track 140. Since the lower track 140 is made of a thermoplastic material the likelihood of the pusher plate 122 galling or binding against the lower track 140 is greatly diminished.

Unlike the prior art surgical stapler of FIGS. 1 and 2, the stack of staples 174 housed within lower chassis assembly 136 is maintained perpendicular relative to lower track 140. The ends of staples 174 are slidably maintained within channels 142 as they are distally advanced to a firing position. As will be discussed later herein, the distal-most staple 174 is aligned to a pre-firing position at an angle generally aligned with the inclination of pusher plate 122 as pusher plate 122 slides under anvil plate 126 and around the periphery of anvil tip 128. The distal-most staple 174 is aligned or turned into firing position by dimples 159 formed along an underside of pusher plate 122.

Figures 6, 7:
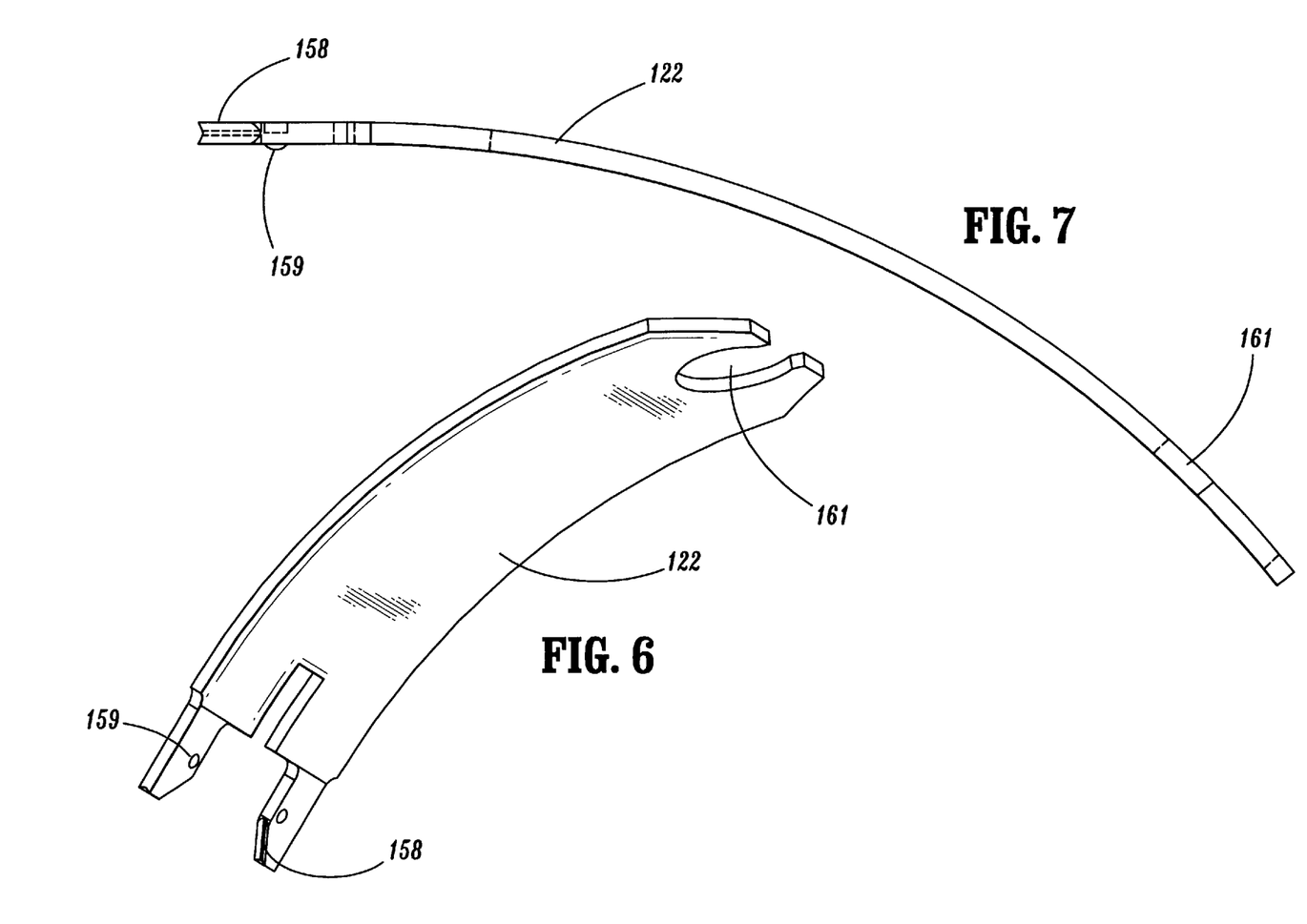
FIG. 6 is an enlarged perspective view illustrating a pusher plate of the cartridge assembly of FIG. 5.
FIG. 7 is an enlarged side view of the pusher plate of FIG. 6.
Figure 8:
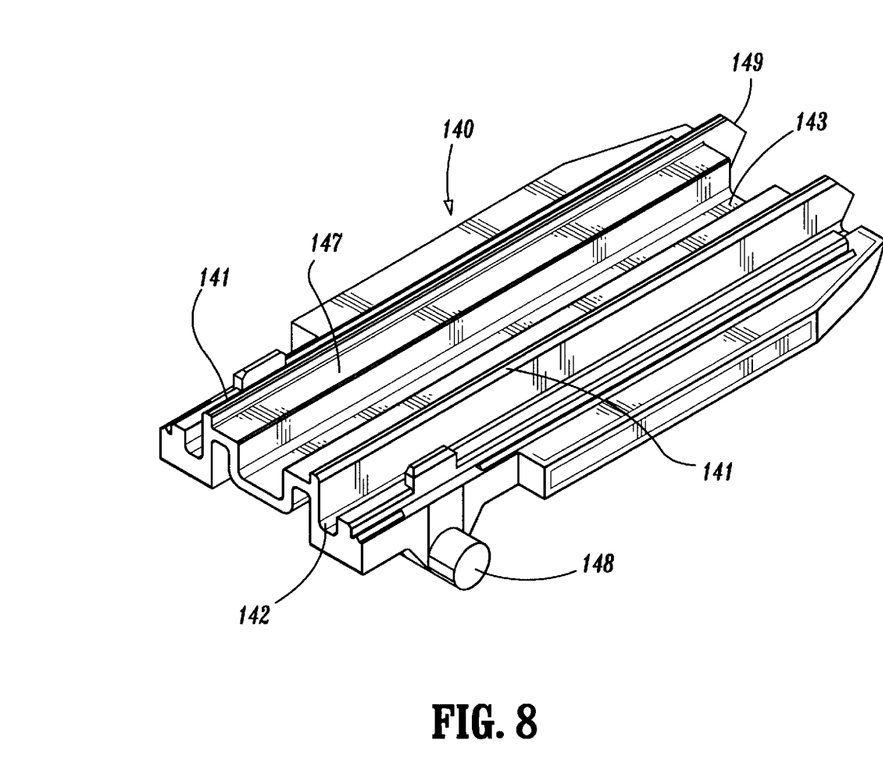
FIGS. 8 and 9 are enlarged perspective views illustrating rear and front views, respectively, of a lower track of the cartridge assembly of FIG. 5.
Figure 9:
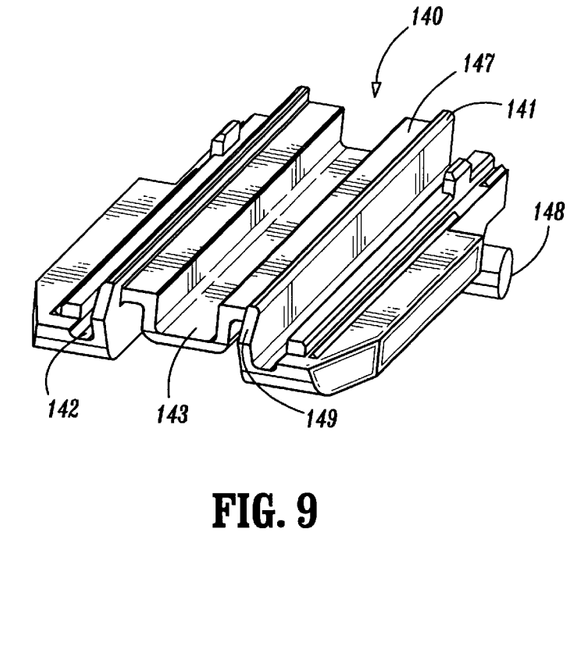

With reference to FIGS. 6 and 7, a preferred embodiment of the pusher plate 122 according to the present disclosure is shown. Pusher plate 122 includes a proximal cut out section 161 for attachment to securing projection 119 and at least one dimple or protrusion 159 along an underside of at least one of the projections 158. The dimples 159 are used to bias or turn the distal-most staple 174 to a firing position as the pusher plate returns to its proximal starting position (FIGS. 11–13).

Figure 12:
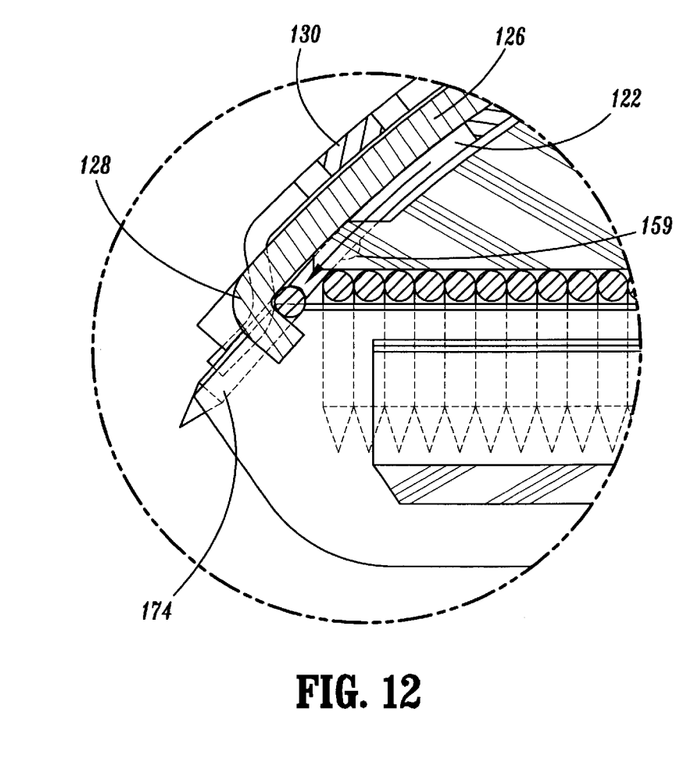
Figure 13:
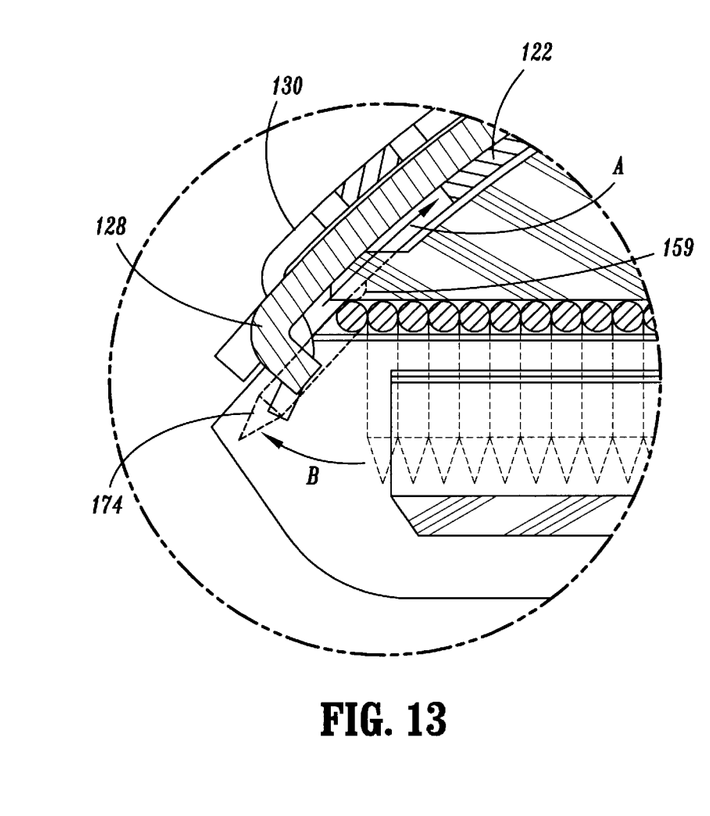
Figure 14:
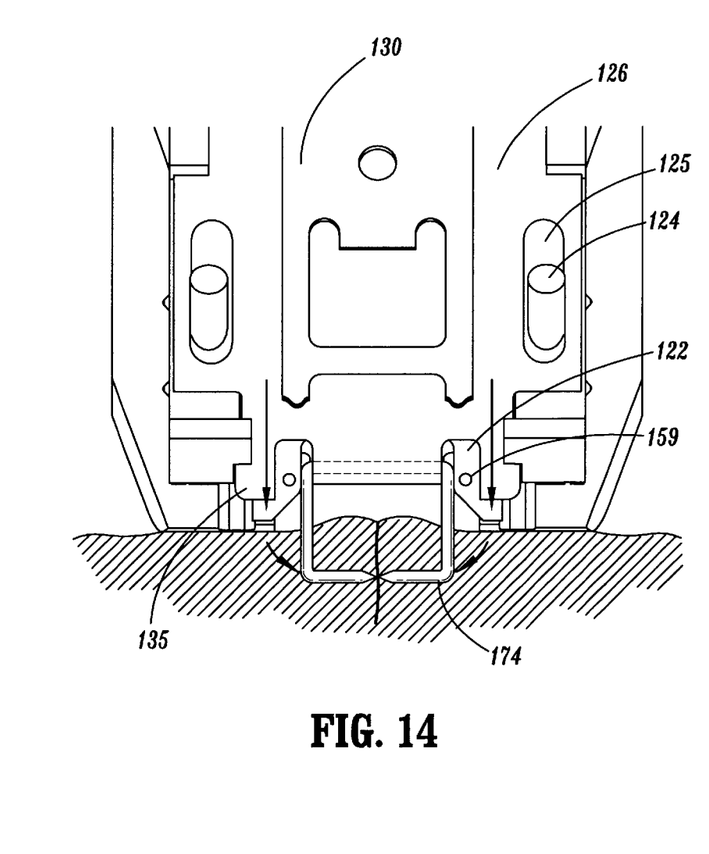
FIG. 14 is an enlarged top view in partial cross-section of the cartridge assembly of the present disclosure illustrating the formation of a staple around tissue.

As best seen FIGS. 11–14, the sequential loading, firing and reloading of a staple 174 of the cartridge assembly according to the present disclosure is shown. A loaded, ready to fire staple 174 is shown at FIG. 11, where a single staple 174 is inclined at an angle generally equal to the inclined angle of pusher plate 122. The firing of staple 174 is generally shown at FIGS. 12 and 14, where pusher plate 122 is advanced distally sliding under anvil plate 126 toward anvil tip 128 to thereby form staple 174 around the periphery of anvil plate 128 (as well as the tissue to be stapled). Once a staple 174 is fired, as shown at FIG. 13, pusher plate 122 is proximally advanced (Arrow A) by the bias of compression coil 120 (as previously described herein) to its pre-firing position. As the pusher plate 122 returns to this pre-firing position, dimples 159 bias, pivot or turn (Arrow B) the distal-most staple 174 from a perpendicular position (as maintained within channels 142 of lower track 140) to a pre-fire position generally aligned with the inclination of pusher plate 122 (see FIG. 11). Hence, by returning to its proximal position, pusher plate 122 by way of dimples 159 reloads a staple 174 into cartridge assembly 100 thereby enabling surgical stapler 160 to deploy additional staples 174 around tissue.

It will be understood that various modifications may be made to the embodiments disclosed herein. For example, pusher plate 122 may include several dimples or protrusions for biasing or turning the distal-most staple 174 to a pre-fire position. Also, cartridge assembly 100 may be employed by a wide variety of surgical staplers not limited to the surgical staplers disclosed herein which are designed to administer staples or fasteners to skin or facia tissue. Therefore, the above description should not be construed as limiting, but merely as exemplifications of preferred embodiments. Those skilled in the art will envision other modifications within the scope and spirit of the claims appended hereto.

What is claimed is:

1. In a surgical fastener applier having a cartridge assembly with an upper chassis and lower track portion mounting a plurality of surgical fasteners in sequentially aligned configuration, each of the surgical fasteners including a crown portion and a pair of end points, a firing assembly for forming surgical fasteners and an actuator for actuating the firing assembly to sequentially form a surgical fastener from the plurality of surgical fasteners, the improvement comprising a thermoplastic lower track portion fixed directly to the upper chassis, the thermoplastic lower track portion having at least one channel with a base, and being configured to support the plurality of sequentially aligned surgical fasteners in a substantially vertical position such that the end points of the surgical fasteners are disposed in the at least one channel and above its base.

2. The surgical fastener applier according to claim 1, wherein the at least one channel includes a pair of channels, each channel having a base and receiving the end points of the plurality of surgical fasteners.

3. The surgical fastener applier according to claim 2, further comprising a surgical fastener follower for distally biasing the plurality of surgical fasteners along the channels of the lower track portion.

4. The surgical fastener applier according to claim 1, wherein the firing assembly includes a pusher plate, the pusher plate having at least one protrusion for biasing at least one of the plurality surgical fasteners to a pre-fire position.

5. The surgical fastener applier according to claim 4, wherein the lower track portion further includes angled distal ends for slidingly receiving distal end projections of the pusher plate.

6. The surgical fastener applier according to claim 3, wherein the at least one protrusion is a dimple.

7. The surgical fastener applier according to claim 4, wherein the at least one protrusion is for biasing the at least one surgical fastener from its substantially vertical position to the pre-fire position in which the end points of the at least one surgical fastener are disposed at a distally directed downward angle relative to the longitudinal axis of the lower track portion.

8. The surgical fastener applier according to claim 7, wherein the cartridge assembly has a distal end, the plurality of surgical fasteners includes a distal most surgical fastener, and the at least one protrusion is for biasing the distal most surgical fastener.

9. The surgical fastener applier according to claim 1, wherein the plurality of surgical fasteners are received along ridge portions of the lower track portion, the lower track portion further including projections for pivotable mounting to the surgical fastener applier.

10. The surgical fastener applier according to claim 1, wherein the lower track portion is monolithically formed.

11. A cartridge assembly for use in a fastener applier having a central body portion and trigger handle, the cartridge assembly comprising:

an upper chassis assembly having a cartridge housing, the cartridge housing including a centrally disposed channel, the channel accommodating a reciprocating pusher follower;

a pusher plate coupled to the pusher follower the pusher plate being movable between advanced and retracted positions and being advanceable against an anvil plate, the pusher plate including at least one protrusion positioned on a distal end thereof, the protrusion being positioned to engage and turn at least one fastener to a pre-fire position as the pusher plate is moved from the advanced to the retracted position; and a lower track portion coupled to the cartridge housing having a plurality of fasteners longitudinally housed therebetween, the lower track portion including a plurality of channels for receiving the plurality of fasteners, wherein at least one of the plurality of fasteners is advanceable between the pusher plate and the anvil plate for forming the at least one fastener around the anvil plate.

12. The cartridge assembly according to claim 11, wherein the lower track is formed of a thermoplastic material.

13. The cartridge assembly according to claim 11, wherein the lower track portion further includes angled distal ends for slidingly receiving distal end projections of the pusher plate.

14. The cartridge assembly according to claim 11, further comprising a fastener follower for distally biasing the plurality of fasteners along at least two of the plurality of channels of the lower track.

15. The cartridge assembly according to claim 11, wherein the pusher plate forms at least one of the plurality of fasteners around an anvil tip of the anvil plate.

16. The cartridge assembly according to claim 11, wherein the at least one protrusion is a dimple.

17. The cartridge assembly according to claim 11, wherein the plurality of fasteners are supported along ridge portions of the lower track, the lower track further including projections for pivotable mounting to a trigger handle of a surgical fastener applier.

18. The cartridge assembly according to claim 11, wherein the lower track is monolithically formed.

19. The cartridge according to claim 11, wherein the protrusion is positioned to pivot at least one fastener as the pusher plate is moved from the advanced position to the retracted position.

20. A staple cartridge for applying staples to tissue, the staple cartridge adapted for use in a surgical stapler having a body portion and a handle portion, the staple cartridge comprising:
- an upper chassis assembly configured and dimensioned to be housed within a surgical stapler, the upper chassis assembly including a reciprocating pusher plate having at least one protrusion along a distal end thereof for biasing at least one staple to a pre-fire position,
- a pusher follower coupled to the pusher plate and housed within the upper chassis, the pusher follower being distally advanced by actuation of a handle portion of the surgical stapler;
- an anvil plate being securely fastened to the upper chassis assembly, the anvil plate including an anvil tip, wherein the pusher plate is distally advanced by the pusher follower against the anvil tip to thereby form the at least one staple from its pre-fire configuration to a formed configuration; and
- a staple carrying lower track coupled to the upper chassis assembly, the lower track including channels for receiving end points of a plurality of staples housed therein each channel having a base, the staple carrying lower track being configured to support the plurality of staples in a substantially vertical orientation with the end points in the channels spaced from their bases.

21. The staple cartridge according to claim 20, further comprising a staple follower for distally biasing the plurality of staples, the staple follower being received within the channels of the lower track.

22. The staple cartridge according to claim 20, wherein the pusher plate further includes distally extending projections which extend distally of the anvil tip when the at least one staple is in the formed position.

23. The staple cartridge of claim 22, wherein the at least one protrusion is located on at least one of the distally extending projections of the pusher plate.

24. The staple cartridge according to claim 20, wherein the lower track portion further includes angled distal ends for slidingly receiving distal end projections of the pusher plate.

25. The staple cartridge according to claim 20, wherein the lower track is formed of a thermoplastic material.

26. The staple cartridge according to claim 20 wherein the at least one protrusion is a dimple.

27. The staple cartridge according to claim 20, wherein the plurality of staples are received along ridge portions of the lower track, the lower track further including projections for pivotable mounting to the hand portion of the surgical stapler.

28. The cartridge assembly according to claim 20, wherein the lower track is monolithically formed.

* * * * *